United States Patent [19]

Selinfreund

[11] Patent Number: 5,753,511
[45] Date of Patent: May 19, 1998

[54] AUTOMATED FINGERPRINT METHODS AND CHEMISTRY FOR PRODUCT AUTHENTICATION AND MONITORING

[75] Inventor: Richard Selinfreund, Branford, Conn.

[73] Assignee: Lion Laboratories, Inc., Old Saybrook, Conn.

[21] Appl. No.: 642,927

[22] Filed: May 6, 1996

[51] Int. Cl.$^6$ ............................................. G01N 21/64
[52] U.S. Cl. ........................... 436/20; 436/24; 436/172
[58] Field of Search ............................ 436/56, 20, 24, 436/22, 23, 2, 172

[56] References Cited

U.S. PATENT DOCUMENTS

| | | | |
|---|---|---|---|
| 1,822,098 | 9/1931 | Huntress | 436/56 |
| 2,265,196 | 12/1941 | Riley | 436/56 |
| 4,387,112 | 6/1983 | Blach | 436/56 |
| 4,439,356 | 3/1984 | Khanna et al. | 436/172 |
| 4,966,856 | 10/1990 | Ito et al. | 436/172 |
| 5,049,673 | 9/1991 | Tsien et al. | 546/107 |
| 5,128,243 | 7/1992 | Potter et al. | 435/7.92 |
| 5,272,090 | 12/1993 | Gavish et al. | 422/82.08 |
| 5,279,967 | 1/1994 | Bode | 436/56 |
| 5,429,952 | 7/1995 | Garner et al. | 436/518 |
| 5,525,516 | 6/1996 | Krutak et al. | 436/56 |
| 5,545,567 | 8/1996 | Gretillat et al. | 422/82.08 |

OTHER PUBLICATIONS

Constant et al., ACS Abstract, Issue of Chemical and Engineering News, Aug. 25, 1994.
Minta et al., J. Biol. Chem. 264:8171, 1989.
AOAC Official Methods of Analysis, 1990, pp. 752–754.
Practical Fluorescence, Second edition, G.G. Guilbault, Editor, Marcel Dekker, Inc., 1990, p. 32.
Dragoco Report, 1990, pp. 12–13.
Chan et al., Biochem. Biophys. Acta 204:252, 1970.
Flow cytometry in food microbiology, R.R. Raybourne, FDA 1996 IFT symposium, Jun. 21–22, 1996.
Molecular fingerprinting of food bourne pathogens, T.J. Barrett, CDC, IFT symposium, Jun. 21–22, 1996.
Coons et al., J. Exp. Med. 91:1–14, 1950.
Glabe et al., Anal. Biochem. 130:287–294, 1983.

*Primary Examiner*—Jeffrey Snay
*Attorney, Agent, or Firm*—Wolf, Greenfield & Sacks, P.C.

[57] ABSTRACT

Highly efficient, low cost, methods and compounds to determine product authenticity, tampering, manufacturing compliance are provided. The methods and chemicals defined are capable of measuring the relative amounts of key materials in these products. The compounds are light-emitting and interact with key elements in products like, neutral spirits, vodka, tequila, soft drinks and infant formulas. After the interactions are complete, methods are employed to determine resulting key components by light emission.

30 Claims, 2 Drawing Sheets

AUTOMATED FINGERPRINT METHODS AND CHEMISTRY FOR PRODUCT AUTHENTICATION AND MONITORING

BACKGROUND OF THE INVENTION

This invention is in the general field of methods, reagents, and apparatus for authenticating or monitoring sample composition.

Authenticating and monitoring products to discriminate between very similar complex mixtures is useful for various reasons. First, the use of counterfeit substances (e.g., misbranded material from a competitor or misformulated material from a licensee/franchisee) should be detected to preserve the integrity of a brand. Characteristics of a product can be used to identify its lot. Similar methods can be used in quality control tests. Also, product counterfeiting raises serious health and safety issues. In 1995, a counterfeit-labeled version of infant formula reportedly was distributed to 15 states in the continental United States. Counterfeit wine, spirits, perfume, infant formula, soft drinks, cosmetics, and pharmaceuticals are estimated to cost United States businesses 200 billion dollars per year ("The Boston Phoenix," Section One, Dec., 2, 1994).

It is important to develop rapid, cost effective, and enforceable methods to identify fraudulent or tampered products. It is also important to determine manufacturing compliance using automated methods to decrease the amount of time spent identifying fraudulent products. It is desirable to minimize the time required from highly skilled researchers and technicians to conduct and record the results of on-line, off-line, and off-the-shelf product authenticity/compliance tests.

There have been attempts to determine product (e.g., infant formula) authenticity by protein electrophoresis, which requires substantial time (and expense) for set up and analysis. In other industries, e.g. wine and spirits, Fourier-transformed infrared analysis, gas chromatography, pH, raman spectroscopy and other analytical methods have been used or proposed for product authentication (Constant et al., Differentiation of Alcoholic Beverages FT-IR Spectra. An Original Multivariate Approach, ACS Abstract presented at 208th ACS National Meeting, Aug. 25, 1994, published in the Issue of Chemical and Engineering News, 1994).

Biocode, Limited has used fluorescent labeled antibodies to determine ingredients in products.

U.S. Pat. No. 5,429,952 discloses adding light-emissive chemicals to a product for analysis.

The use of standard analytical methods to monitor every lot or batch for a product or competitor product for authenticity or compliance with laboratory equipment can often be costly.

SUMMARY OF THE INVENTION

We have discovered an automated method of developing a database to store information for "fingerprint"-type analysis of products (even as to product lot numbers and batch). The automated analysis is a method of evaluating and discriminating products, even within a narrow field or industry, competing and otherwise, e.g., to establish authenticity or point of origin of the product. The invention relates to an automated method for identifying key ingredients and/or the relative amounts of key ingredients in products. The method allows for authenticating and monitoring products for fraud and quality control using light emission. The invention also relates to light-emissive compounds (e.g., including one or more light-emissive compounds) which can be used to identify and quantitate the relative amounts of key ingredients in products.

In one aspect, the invention features a method for determining relatedness of a sample to a standard known to be authentic or known to have at least one selected characteristic of authentic material. The method includes: a) provides a mixture of sample and least one light-emissive compound ("LEC"); (b) irradiating the sample mixture with an irradiating wavelength of light; (c) monitoring at least one emitted wavelength of light (generated in response to the irradiating) to establish a sample fingerprint; and (d) providing a standard fingerprint characteristic of a standard mixture; and (e) comparing the sample fingerprint with the standard fingerprint to determine whether the sample is authentic. The standard mixture includes the standard and the light-emissive compound. The standard fingerprint is generated by irradiating the standard mixture with the irradiating wavelength and monitoring the emitted wavelength in response thereto.

In preferred embodiments, the method further includes: providing a background control mixture which includes the light-emissive compound without the sample or the standard; irradiating the background control mixture with the irradiating wavelength and monitoring the emitted wavelength in response thereto, to establish background emission; and determining the fingerprint of the sample based on at least one difference between the emission of the control mixture and the emission of the sample mixture. It is preferred that standard be a composition having a predetermined relative amount of a component characteristic of authentic material. The sample fingerprint is generated based on a first change in emission, determined by comparing the background emission and the emission from the sample mixture. The standard fingerprint is generated based on a second change in emission, determined by comparing the background emission and the standard emission. The comparing step includes comparing the first change in emission to the second change in emission, e.g., to quantify relative amounts of sample component.

In other preferred embodiments, the light-emissive compound is added to the sample by an automated pipette. It is preferred that the sample mixture be dispensed by an automated pipette in a multiwell plate.

In other preferred embodiments, the standard, the sample, or both, inherently include a fluorescent, phosphorescent, or luminescent compound. In some products the compound is caffeine.

In other preferred embodiments, the light-emissive compound is fluorescent, phosphorescent, or luminescent, and emission varies in response to quantity or quality of critical product components. Preferably, the light-emissive compound reacts with components of the sample, the standard, or both, to yield at least one fluorescent, phosphorescent, or luminescent component.

In other preferred embodiments, the standard is a composition having a predetermined relative amount of a component characteristic of authentic material, and the comparing step includes quantifying the relative amounts of the component in the sample.

In preferred embodiments, the method includes performing steps (b)-(c) listed above on page 2, at least two times. Steps (b)-(c) may be performed using different light-emissive compounds, and different irradiating and emission wavelengths are monitored in each performed step.

In other preferred embodiments, steps (b)-(c) are repeated at least three times using the same light-emissive compounds and the same irradiating and emission wavelengths to establish a fingerprint emission profile for the product.

In preferred embodiments, the standard is a caffeine-containing beverage, and the light-emissive compound is: a) 5-(2-carbohydrazinomethylthioacetyl) amino-fluorescein; b) 5-(4,6-dichlorotriazinyl)aminofluorescein; c) Fluo-3 pentaammonium salt (Minta et al., J. Biol. Chem. 264:8171, 1989 and U.S. Pat. No. 5,049,673); d) 4-aminofluorescein; e) 5-aminofluorescein; f) sulfite blue coumarin; g) courmarin diacid cryptand (CD222) (Costlei et al., J. of Chem. Society Perkins translation 2, p. 1615); or h) Eosin Y.

In still other preferred embodiments, the standard is an infant formula, and the light-emissive compound is selected from the group consisting of 5-(2-carbohydrazinomethylthioacetyl) aminofluorescein, 5-(4,6-dichlorotriazinyl)aminofluorescein, Fluo-3 pentaammonium salt, or Courmarin benzothiazole, tetrapotassiun salt (BTC-5N) (Cell Calcium, p. 190, 1994). In other preferred embodiments, the standard contains corn syrup, and the light-emissive compound is selected from the group consisting of 5-(2-carbohydrazinomethylthioacetyl) aminofluorescein, 5-(4,6-dichlorotriazinyl) aminofluorescein, Fluo-3 pentaammonium salt, 4-aminofluorescein, 5-aminofluorescein, sulfite blue coumarin, courmarin diacid cryptand (CD222), or Eosin Y. In other preferred embodiments, the standard is an ethanol-containing beverage and the light-emissive compound is selected from the group consisting of 5-(2-carbohydrazinomethylthioacetyl)aminofluorescein, 5-(4,6-dichlorotriazinyl)aminofluorescein, Fluo-3 pentaammonium salt, proflavine hemisulfate, tetra(tetramethylammonium) salt, acridine orange hydrochloride hydrate, BTC-5N, acriflavine, 4-aminofluorescein, or 5-aminofluorescein. Compound 11 is sulfite blue coumarin. Compound 12 is courmarin diacid cryptand (CD222). Compound 13 is Eosin Y. In other preferred embodiments, the standard is an aqueous mixture, and the light-emissive compound is a compound that interacts or reacts with heavy metals, the light-emissive compound being selected from the group consisting of Fluo-3 pentaammonium salt, or BTC-5N.

In another aspect, the invention features a method for determining relatedness of a first sample to a second sample, neither of which is a known standard. The method includes: (a) providing a first sample mixture including the first sample and at least one light-emissive compound; (b) irradiating the first sample mixture with an irradiating wavelength of light; (c) monitoring at least one emitted wavelength of light generated in response to the irradiating, to establish a first sample fingerprint characteristic of the first sample mixture; (d) providing a second sample fingerprint characteristic of a second sample mixture, the second sample mixture including the second sample and the light-emissive compound; the second sample fingerprint being generated by irradiating the second sample mixture with the irradiating wavelength and monitoring the emitted wavelength in response thereto; and (e) comparing the first sample fingerprint with the second sample fingerprint to determine relatedness of the two samples.

In preferred embodiments, the first sample is identified as a specific product or as part of a homogeneous lot of a product by comparing the fingerprint emission profile of the first sample to a library of fingerprint emission profiles of samples whose product composition or lot number are known.

In other preferred embodiments, the method further includes providing an additional fingerprint emission profile for each of at least two additional samples and comparing the first sample mixture fingerprint to each of the additional fingerprint emission profiles.

In preferred embodiments, the method is used to determine product authenticity, product tampering, or product manufacturing compliance. In other preferred embodiments, the sample is a perfume, fragrance, flavor, food, or beverage product.

Light-emissive compounds are involved in light emission in response to irradiation with light of a different wavelength. Light emission of interest can be a result of phosphorescence, chemiluminescence, or, more preferably, fluorescence. Specifically, the term "light-emissive compounds," as used herein, means compounds that have one or more of the following properties: 1) they are a fluorescent, phosphorescent, or luminescent; 2) react, or interact, with components of the sample or the standard or both to yield at least one fluorescent, phosphorescent, or luminescent compound; or 3) react, or interact, with at least one fluorescent, phosphorescent, or luminescent compound in the sample, the standard, or both to alter emission at the emission wavelength.

"Fingerprint," refers to the light emission intensity from a light-emissive compounds in combination with a liquid sample of a product. Accordingly, each product can have a particular fingerprint. A "fingerprint emission profile" is an assembly of fingerprints of a liquid sample of a product in combination with a series (or profile) of different light-emissive compounds.

The term "key ingredient," as used herein, means a component included in a composition of a product that is important in identifying the particular product.

The term "trace compound," as used herein, means a compound that is present in low concentrations (e.g., at ppm or ppb levels) in a product that is related, for example, to a particular key ingredient. The trace compound can be introduced at the source of the key ingredient or during the manufacture of the product.

The invention can include one or more of the following advantages. The method can be used in the distilled spirits industry, where trace compounds and key ingredients can be measured using specific light-emissive compounds. Further, light-emissive compounds that indicate the source of ethanol can be used to determine the authenticity of a product. For example, spirits derived from yellow dent corn contain different trace compounds than spirits derived from cane sugar.

Moreover, although colas, and other soft drinks, contain similar levels of key ingredients, the levels key ingredients can be used to determine whether a particular manufacturer is diluting the concentrate to the appropriate level. For example, caffeine can be a targeted ingredient for light-emissive compounds in the analysis of soft drinks. Additional targets in soft drinks can include, but are not limited to, the high fructose corn syrup and the pH.

Furthermore, perfumes, fragrances, flavors, foods, and all types of beverages can be fingerprinted, using the methods of the invention, without adding any reagents to the product the user is going to consume. The addition of tracer dyes as a strategy for determining authenticity can raise health risks and other problems. The invention allows accurate light-emissive profiles of products to be determined and monitored without altering the product.

Other features and advantages of the invention will be apparent from the following detailed description thereof, and from the claims.

DETAILED DESCRIPTION

Figure 1:
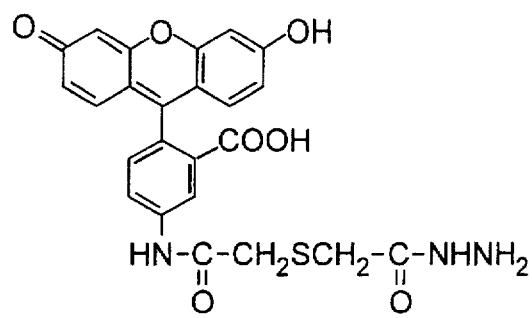
FIGS. 1–13 are drawings that show the chemical structures of compounds 1–13, repectively.
Figure 2:
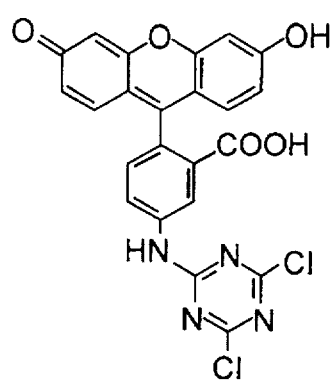
Figure 3:
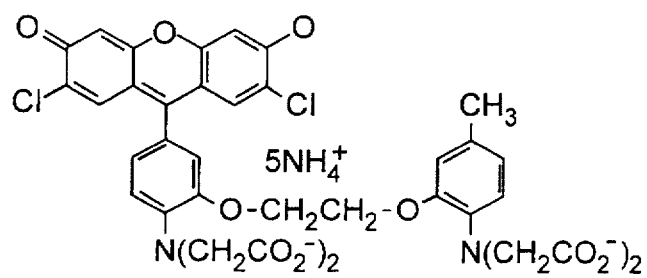
Figure 4:
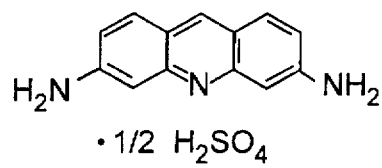
Figure 5:
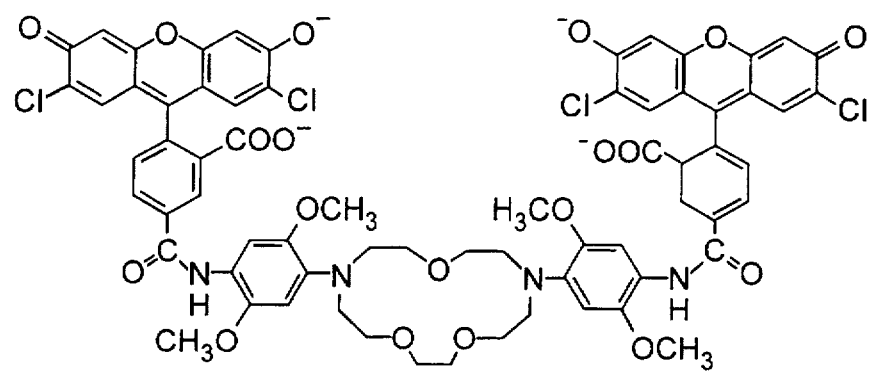
Figure 6:
Figure 7:
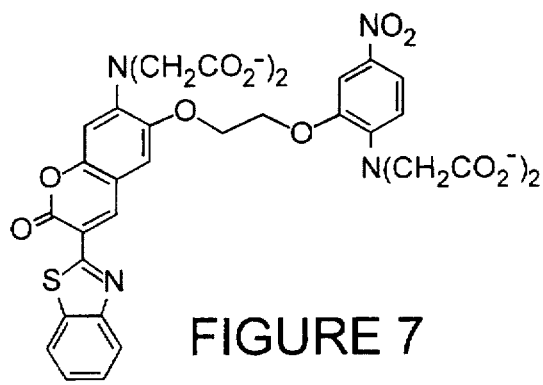
Figure 8:
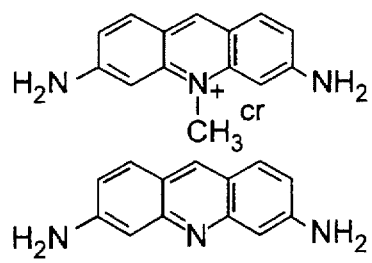
Figure 9:
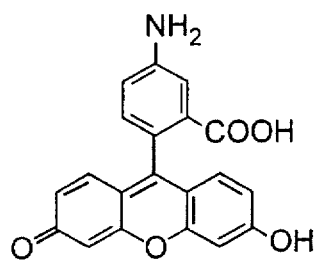
Figure 10:
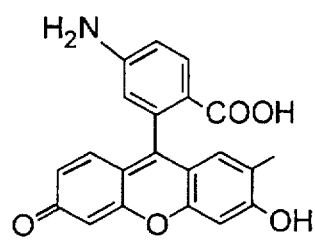
Figure 11:
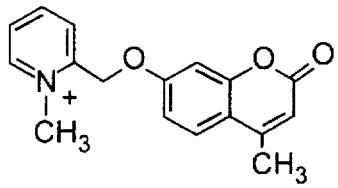
Figure 12:
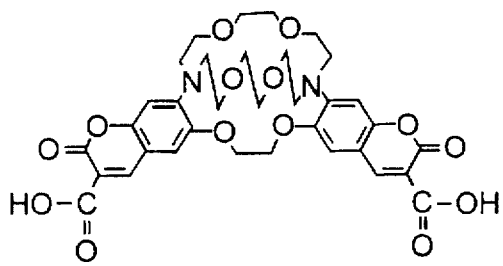
Figure 13:
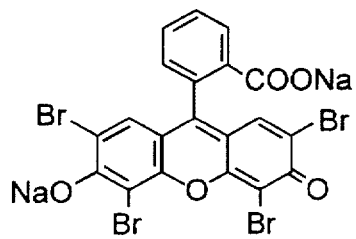

The invention features an automated method for analyzing key ingredients and the relative amounts of key ingredients in products which in turn enables authentication and monitoring products for fraud and quality control. Particular light-emissive compounds can be used to identify and quantitate the relative levels of key ingredients in the products.

One method for identifying counterfeit or altered products relies on the development of a group of between two and seven specific light-emissive compounds for a single product along with specialized automated handling methods and new data analysis. These methods can be used to provide a method which is simpler to use than prior techniques and which can be performed rapidly using conventional and generally available equipment. It is a further aspect of the invention to provide a technique which gives quantitative measure of the degree to which the product is altered or tampered with. It is a further aspect of the invention to provide methods and compounds for identifying key product ingredients.

The invention provides a method for determining the relative amounts of key ingredients in a product by exposing the products to selected light-emissive compounds present in a light-emissive compound. The key ingredients are selected so that in the presence of the product, the compounds can partition, intercalate, or bind to the key ingredients in the aqueous and/or organic liquid fractions of the product. The interaction between the components of the product and the light-emissive compound induces a chemical change that can be detected using automated light-emissive detection systems. Light-emission can include luminescence, fluorescence, or phosphorescence. Fluorescence is described, for example, in "Practical Fluorescence," Second Edition, G. G. Guilbault, Editor, Marcel Dekker, Inc., 1990, which is incorporated herein by reference.

In general, a sample of the product and the light-emissive compound are mixed. The light-emissive compounds and key ingredients in the product are allowed to react for a period of time and temperature that is specific for each product and light-emissive compound, for example, until light emission from the mixture no longer changes with time. Bandpass and cutoff filters are used to isolate excitation wavelengths from emission spectra due to light emission from the sample. Change in light emission due to the presence of the product can be determined from the formula [(Fd-Fp)/Fd]×100, where the light emission of the light-emissive compound in the absence of product is Fp, and the light emission after exposing the light-emissive compound to the product is Fd. The light emission changes as a result of interactions of the light-emissive compound with species in the product.

The light-emissive compound can include two light-emissive compounds and can be added together in the same sample well, if the emission maximum of the dyes is more than 40 nm apart. The wavelength filter must be changed for each light-emissive compound being observed. There is no practical limit to the number of light-emissive compounds that can be used to demonstrate the specific presence of a particular trace compound. The number of light-emissive compounds can be increased to indicate the specific presence of an ingredient or to rule out possible non-specific analysis of closely related compounds.

It is possible to determine the authenticity of product if the trace or chemical structure of the product is unknown by using between four and seven individual light-emissive compounds in the light-emissive compound. Using an automated robotics workstation (e.g., the Beckman Biomek 1000), it is possible to combine the light-emissive compounds in random order with the product standards in a microwell plate. Once a detectable light emission pattern is developed for all the standards, a single test product can be added to the same microwell plate (e.g., up to 99 standards and 1 single test product). The light emission output of the sample is compared to each of the standards on the plate run. In this way, it is possible to determine authenticity without developing a prior record of standard light emission levels.

There are many examples of light-emissive compounds that can be included in the light-emissive compound, some of which are shown in FIG. 1 (Compounds 1–13). Compound 1 is 5-(2-carbohydrazinomethylthioacetyl) aminofluorescein. Compound 2 is 5-(4,6-dichlorotriazinyl) aminofluorescein. Compound 3 is Fluo-3 pentaammonium salt. Compound 4 is proflavine hemisulfate (3,6-dimethylaminoacridine hemisulfate). Compound 5 is tetra (tetramethylammonium) salt. Compound 6 is acridine orange hydrochloride hydrate. Compound 7 is BTC-5N. Compound 8 is acriflavine. Compound 9 is 4-aminofluorescein. Compound 10 is 5-aminofluorescein. Compound 11 is sulfite blue coumarin. Compound 12 is courmarin diacid cryptand (CD222). Compound 13 is Eosin Y.

Some examples of the liquid products that can be analyzed and the light-emissive compounds that can provide distinctive and significant analyses of the products are: alcohol-based products such as neutral spirits, vodka, and tequila that can be analyzed, for example, with Compounds 1, 2, 3, 4, 5, 6, 7, 8, or 9; sucrose and high fructose based products such as soft drinks (e.g., Coca-Cola and Pepsi) that can be analyzed, for example, with Compounds 1, 2, 3, or 9; and infant formulas such as Similac, Carnation, Enfamil that can be analyzed, for example, with Compounds 1, 2, 3, or 7.

The methods of the invention can be used to analyze other liquid products as well as liquid samples derived from other products, based on the correct choice of light-emissive compounds used in the analysis. For example, light-emissive compounds that are amine-containing (e.g., Compound 1) and light-emissive compounds that are reagents for modifying amines, alcohols, arginine, guanosine, and polysaccharides (e.g., Compound 2) can be used in product authenticity/monitoring and testing of, for example, neutral spirits, distilled spirits, infant formula, or soft drinks. In addition, light-emissive chemicals that are calcium indicators (e.g., Compound 3) or are capable of complexing with $Cd^{2+}$, $Zn^{2+}$, $Pb^{2+}$ and $Ba^{2+}$ (e.g., Compound 7) can be used for product authenticity/monitoring testing of neutral spirits, distilled spirits, or soft drinks. Light-emissive acridine compounds (e.g., Compound 6) are capable of complexing with lipids and fats for product authentication or monitoring of distilled spirits or infant formulas. Light-emissive acriflavine compounds that interact with alcohols (e.g., Compound 8) are useful for product authentication/monitoring testing of neutral and distilled spirits. Light-emissive chemicals that react with primary alcohols, aldehydes or ketones (e.g., Compounds 9 and 10) are useful for authentication or monitoring of neutral spirits, distilled spirits, or soft drinks.

Selection of Light-Emissive Compounds

Light-emissive compounds containing one or more light-emissive compounds can be selected, in general, based on the following guidelines: (1) a light-emissive compound in the composition should react with a key ingredient in the product; (2) a light-emissive compound in the composition should react (or interact) with a key ingredient in the product in a concentration dependent manner; (3) the light-emissive compound and the reaction products should be stable and the reaction should be repeatable; (4) similar lot numbers of the product should react (or interact) exactly the same way with the light-emissive compound; and (5) the light-emissive compound should react (or interact) differently with closely related products on the basis of the chemical structures of key ingredients in the product (e.g., to discriminate between brand names of a product, such as between, for example, Smirnoff and Absolute vodkas). In many situations, it is desired that multiple light-emissive compound(s) be identified to authenticate or monitor a single consumer product.

To determine a light-emissive compound that can be used in the analysis of a product, the chemical structure of key ingredients in the selected product are chosen, or assumed to be present in the product. At least one key ingredient is targeted in a particular product. A candidate light-emissive compound can generally be selected using the guidelines, described above, along with the information listed in Table 1 and Table 2. The information listed in the tables is not intended to be limiting, but provides general information that can be useful in the selection of a light-emissive compound. Table 1 lists reactive groups in light-emissive compounds that can be useful for identifying particular functional groups in a key ingredient of the product. Table 2 lists selected useful initial light-emissive compounds. The light emission from a sample containing a light-emissive compound [selected according to the guidelines as a result of reactions (or interactions) with key ingredients in the product] can be used to authenticate and monitor products for fraud and quality control.

TABLE 1

| light-emissive compound reactive group | key ingredient functional groups |
|---|---|
| activated ester | amines or anilines |
| acyl azide | amines or anilines |
| acyl halide | amines, anilines, alcohols or phenols |
| acyl nitrile | alcohols or phenols |
| aldehyde | amines or anilines |
| alkyl halide | amines, anilines, alcohols, phenols or thiols |
| alkyl sulfonate | thiols, alcohols or phenols |
| anhydride | alcohols, phenols, amines or anilines |
| aryl halide | thiols |
| aziridine | thiols or thioethers |
| carboxylic acid | amines, anilines, alcohols or alkyl halides |
| diazoalkane | carboxylic acids |
| epoxide | thiols |
| haloacetamide | thiols |
| halotriazine | amines, anilines or phenols |
| hydrazine | aldehydes or ketones |
| hydroxyamine | aldehydes or ketones |
| imido ester | amines or anilines |
| isocyanate | amines or anilines |
| isothiocyanate | amines or anilines |

TABLE 2

| light-emissive compound | analyte |
|---|---|
| acridine orange | |
| acid alizarin Garnet R | alcohol |
| 9-amino acridine | ethanol |
| anthracene | ethanol |
| chlorophyll A | ethanol/methanol |
| chlorophyll B | methanol |
| eosin | |
| FAD | |
| indole | |
| naphthalene | alcohol |
| NADPH | |
| proflavine | |
| protoporphyrin I | |
| pryodoxal | |
| pyridoamine-5-phosphate | |
| quinacrine | |
| quinine | |
| 6-methoxyquinoline | |
| phenanthrene | alcohol |
| resorcinol | |
| rhodamine 3G (or 6G) | |
| riboflavin | |
| salicylic acid | |
| serotonin | |
| skatole | |
| sulfanilic acid | |
| sodium salicylate | water |

Another light-emission tool for product identification is the standard light emission phenomenon called impurity quenching. Even in dilute solutions, impurities can cause measurable quenching of light emission. The specific amount of quenching can be exploited to identify a specific lot or batch of a product. See, for example, "Practical Fluorescence," G. G. Guilbault, Editor, page 32. It is also possible that the light emission wavelength of the light-emissive compound can shift in the presence (or absence) of an ingredient in the product. This shift can be used to quantify the amount of ingredient present in the product.

Regional production differences can be determined using two different methods. One method involves identifying compounds of regional specificity from differences in starting materials. Different suppliers of ingredients in a product will leave different levels of trace compounds in their supplied materials. Even though these trace compounds are present at extremely low levels, the light-emissive compounds are sensitive to a level of parts per million and even to parts per billion in some cases. For example, the trace levels of compounds, such as aldehydes and methanol, can be used to identify different varieties (i.e., suppliers) of sucrose and high fructose corn syrup in fruit and cola consumer products. In another example, ethanol distilled from corn contains different trace components than ethanol distilled from cane sugar. The identification and analysis of these trace elements can be used to detect product authenticity or detect backfilling (dilution) of a particular product.

A second method of determining regional differences in a product involves analysis of trace elements (or compounds) in, for example, the water used to dilute the consumer product. The trace elements (or compounds) can be used as a specific lot number marker. Specifically, levels of calcium, magnesium and/or heavy metals can be used to identify products by "specific lot number water identity." Additionally, a company's processes can result in a detectable amount of at least one other trace material that can identify the companies specific product. The identity and quantity of the trace materials make it possible to identify the lot number of a specific production run. For example, many colas have a fixed level of caffeine in the concentrate and in the final product. Light-emissive compounds that indicate caffeine concentrations can be developed according to methods described herein.

The relative amounts of key ingredients in a sample can be determined by light emission analysis. The light emission measurement can be used in combination with other trace light emission analysis to determine authenticity. For example, vodka must contain 50% ethanol to legally be called vodka. Additionally, this method can be used to identify a lot number or batch number or to determine the authenticity of, for example, orange juice, apple juice, or lemon juice.

The relative amounts of water can be compared in a standard sample standard and a suspect sample using, for example, the naphthylamine light-emissive dyes. Sulfonated naphthylamines, such as 2-p-toludinylnaphthalene-6-sulfonate (2,6-TNS) and 1-anilino-8-naphthalenesulfonate (1,8-ANS), shift light emission wavelength in water. The relative amount of shift depends on the amount of water in a sample. For example, in water, the spectral sensitivity is substantially shifted to longer wavelengths, and the light emission quantum yield and decay times decrease.

Data Analysis

Multi-variant analysis can be used to analyze the light emission results of each product sample with each light-emissive compound. Typically, the results are interpreted in comparison to light emission from a standard product sample treated in the same way, or a "fingerprint." All samples can be analyzed for the presence of key ingredient using a light-emissive compound containing a single light-emissive compound or a combination of light-emissive compounds. The largest and smallest mean values are determined for each set of product samples using four independent measurements made of the same sample (n=4). The multiple comparison procedure allows the determination of a critical value (e.g., at a 95% confidence level) for the difference between the largest and the smallest sample means, which relates to the differences in the respective products. A difference in the sample means, that is equal to or greater than the critical value, suggests a significant difference in the products. A significant difference can imply different product treatments, starting materials and compositions.

Typically, the analysis involves Tukey Multiple Comparison Procedure conducted, e.g., at a 95% confidence level ($\alpha=0.05$). The Multiple Comparison Procedure assumes that the number of sample means, k, are based on independent random samples, each containing the same number of observations, n. In this case, s, the standard deviation is the square root of the mean square errors (MSE) of the sample means. The MSE has a number of degrees of freedom, v, associated with it. From k, v, and $\alpha$, the critical value of the Studentized range, $q_\alpha(k,v)$, can be determined. It then follows that the distance, omega ($\omega$) is $$\omega = q_\alpha(k,v) \frac{s}{n^{0.5}}$$

Tukey analysis can allow the identification of sample means that do not match the standard products. If two measurements differ by a value greater than omega, then the two samples are different. If not, the samples are pairs have substantially similar compositions (i.e., are the same composition, but could be different batches).

Each light-emissive compound/product sample system can be considered a single variant. Combining the analyses for each of the light-emissive compounds together can lead to a multi-variant analysis program that we have developed a software program for. This multi-variant light-emissive product authenticity analysis can be carried out using, for example, spread-sheet type computer programs.

Materials and Methods

The methods were developed to optimize analysis or determine the authenticity or tampering of a product in the water and/or organic component of the product. The general methods for using Compounds 1–10 are generally described below.

Beckman Biomek 1000 automated workstation (Beckman Instruments, Columbia, Md.) was used to make dilutions and place 150 microliters of the light-emissive compound into a test plate, although any automated dispensing workstation can be used. The test plate can be made from any suitable material and can have any number of wells, such as 6, 24, 96 or 384 wells (Corning-Costar, Falcon-Collaborative, microwell test plates). The light emission of the light-emissive compound in the absence of product is Fp, and the light emission after exposing the light-emissive compound to the product is Fd. The Fd and Fp light emission analysis for the purpose of these experiments was made using a Molecular Dynamics FluorImager 575, but any microplate reader can be used (e.g., Cytofluor). Bandpass and cutoff filters are used to isolate excitation wavelengths from emission spectra due to light emission from the sample. Fd light emission analysis was made for each chemical in each well of the test plate. Repetition of measurements allows correction for systematic variability due, for example, to automatic pipetting (<5%). Next, 150 microliters of product are added to the chemicals in the microwells using the Beckman Biomek 1000 automated workstation. The chemical and the product are allowed to react for a period of time and temperature that is specific for each product and chemical. Change in chemical light emission due to the presence of the product is determined by calculation using the equation $[(Fd-Fp)/Fd] \times 100$.

Compound 1, 5-(2-carbohydrzinomethylthioacetyl)-aminofluorescein, was obtained from Molecular Probes, Inc., Eugene, Oreg., Lot 2841-1. The final concentration of the working solution can range between 0.5 and 10 micromolar. Compound 1 has an excitation maximum at 488 nm at neutral pH and 356 nm at pH 8. Compound 1 has an emission maximum at 520 nm. See, R. E. Hileman, et al., Bioconjugate Chem. 5:436 (1994) for the synthesis of the compound.

Compound 2 and Compound 3 should be used in the method together. Compound 2, 5-(4,6-dichlorotriazinyl)-aminofluorescein, was obtained from Molecular Probes, Inc., Eugene, Oreg., Lot 2851-1. A stock solution of Compound 2 was prepared in dimethyl sulfoxide (DMSO, ACS reagent, Sigma Chemical, St Louis, Mo.). The final concentration of the working solution can range between 0.5 and 10 micromolar. Compound 2 has an excitation maximum at 495.7 nm and emission maximum at 516.3 nm. For a reference that describes the original use of this compound, see, Barskii et al., Izv. Akad. Nuak SSSR, V. E. (1968) PN 101.

Compound 3, Fluo-3, pentaammonium salt, was obtained from Molecular Probes, Inc., Eugene, Oreg., Lot 2641-6. The final concentration of the working solution can range between 0.5 and 10 micromolar. Compound 3 has an excitation maximum at 510 nm and emission maximum at 530 nm. Fluo-3 was developed for measuring calcium levels in cellular experiments. See, for example, Tsien, R., et al., J. Biol. Chem. 264:8171 (1989).

Compound 4, proflavine hemisulfate (3,6-diaminoacridine hemisulfate) was obtained from Sigma-Aldrich, St. Louis, Mo. The final concentration of the working solution can range between 0.5 and 10 micromolar. Compound 4 has an emission maximum at 515 nm in methanol. Proflavine was developed as a fabric dye and for cell staining procedures. See, for example, Chan, L. M., et al., Biochem. Biophys. Acta, 204:252 (1970).

Compound 5, tetra(tetramethylammonium) salt, was obtained from Molecular Probes, Inc., Eugene Oreg. The final concentration of the working solution can range between 0.5 and 20 micromolar, depending on the product tested. Compound 5 has an excitation maximum at 488 nm and an emission maximum around 535 nm. Compound 5 was developed at Molecular Probes as Sodium Green™ for the fluorometric determination of $Na^+$ concentrations.

Compound 6, acridine orange hydrochloride hydrate, obtained from Sigma-Aldrich, St. Louis, Mo. The final concentration of the working solution can range between 0.5 and 20 micromolar. Compound 6 has an excitation maximum at approximately 490 nm and emission maximum at 519 nm. Compound 6 can be used for printing inks and as a stain for fats and lipids in biological samples. See, for example, Clark, G., "Staining Procedures," ed. Williams and Wilkins, Baltimore 1981 pp. 48, 57, 61, 71, 72, 86, 87, 89, 90, and 429.

Compound 7, BTC-5N (Costlei et al., J. of Chem. Society Perkins translation 2, p. 1615), was obtained from Molecular Probes, Inc., Eugene, Oreg. The final concentration of the working solution can range between 0.5 and 20 micromolar. Compound 7 has an excitation maximum at approximately 415 nm and an emission maximum at 515 nm.

Compound 8, acriflavine, is composed of an approximate 8 to 1 mixture of 3,6-diamino-10-methyl-acridinium chloride and 3,6-diaminoacridine, and was obtained from Sigma-Aldrich, St. Louis, Mo. The working solution concentration can range between 0.5 and 20 micromolar, depending on the product tested. Compound 8, in its neutral form, has an excitation maximum in ethanol at 483 nm and an emission maximum at 517 nm with a long-lasting emission state that can be used to identify the relative levels of ethanol in a sample. The long-lasting emission in ethanol is noted by Furumoto, H. W. and Ceccon, H. L., IEEE J. Quantum Electron., QE-6, 262, (1970). Compound 8 is an ordinary biological stain and is useful as a light-emissive compound and a Schiff reagent. See, for example, "Conn's, Biological Stains," 9th ed.: Lillie, R. D., Ed.; Williams and Wilkins: Baltimore, 1977; p. 355.

Compound 9, 4-aminofluorescein, was obtained from Sigma-Aldrich, St. Louis, Mo. The working solution concentration can range between 0.5 and 20 micromolar, depending on the product tested. Compound 9 has an excitation maximum at 496 nm and an emission maximum at 530 nm. See, for example, Coons, A. H., et al., J. Exp. Med. 91:1-14 (1950).

Compound 10, 5-aminofluorescein, obtained from Sigma-Aldrich, St. Louis, Mo., was used in a similar manner and at similar concentrations as Compound 9. The emission is at 530 nm. Glabe et al. Anal. Biochem. 130:287-294 (1983).

Compound 11, sulfite blue coumarin, S-6902, was obtained from Molecular Probes, Eugene, Oreg. Compound 11 has an excitation maximum at 325 nm and an emission maximum at 373 nm. Compound 11 can be useful for measuring sulfites. Sulfite contamination in high fructose corn syrup is a problem well known in the corn processing and milling industry.

Compound 12, courmarin diacid cryptand (CD222) (Costlei et al., J. of Chem. Society Perkins translation 2, p. 1615), was obtained from Molecular Probes, Eugene Oreg. Compound 12 is a ratio dye with an excitation maximum at 365 nm and emission maximum at 465 nm. Compound 12 is a potassium sensitive dye, enabling authentication based potassium benzoate, a preservative in many cola drinks.

Compound 13, Eosin Y, was obtained from Sigma-Aldrich, Certified Grade, St. Louis, Mo. Compound 13 has an excitation maximum at 522 nm and an emission maximum at 551 nm. Compound 13 is a pH-sensitive light-emissive compound.

EXAMPLE 1-NEUTRAL SPIRITS

The analysis methods of the invention can be used in the wine and distilled spirits industry to determine product authenticity, defend international trademarks, document product quality, and detect product backfilling (i.e., dilution with lower quality ingredients). In this industry, the origin and source of the ethanol in a product can be used to determine product authenticity. The product label must correctly represent the contents in a manufacturer's bottle. Previously, there was no practical method for determining the source of ethanol or neutral spirits (96% ethanol).

A double blind experiment was conducted to determine the differences between 6 neutral spirits samples. In addition, if there were duplicates, the experiment was designed to identify the duplicates.

The neutral spirits product origins can be identified from the data presented in Table 3 and Table 4. Referring to Table 3, the level of light emission upon excitation was monitored in an array of six samples (10-1, 10-2, 10-3, 10-4, 10-5, and 10-6) that were each tested four times (A, B, C, and D) with a pair of light-emissive compounds. Within each set, each sample of the product was tested four times with a light-emissive compound. The excitation wavelength was 522 nm. The light-emissive compounds were Compound 2 and Compound 3.

Stock solutions of the light-emissive compounds were prepared by dissolving Compound 2 in DMSO at a concentration of 2 mM and Compound 3 in DMSO at a concentration of 1 mM.

The concentrations of the working solutions of light-emissive compounds were optimized against known samples of neutral spirits. The optimum concentrations were determined from the concentrations of light-emissive compounds that provides emission intensities that are capable of discriminating known neutral spirits samples from other samples by a value greater than omega. The working solution of Compound 2 was prepared by diluting 120 µL of the stock solution dye in 20 mL of distilled water. The working solution of Compound 3 was prepared by diluting 100 µL of the stock solution in 20 mL of distilled water.

Both Compound 2 and Compound 3 require a 530BP±15 nm band pass filter to reduce the excitation wavelength intensity during the emission measurements. The intensity of the emission was measured in relative fluorescence units

TABLE 3

| | STATISTICAL DATA | | | | NEUTRAL SPIRITS | | | |
|---|---|---|---|---|---|---|---|---|
| | A 10-1 | A 10-2 | A 10-3 | A 10-4 | A 10-5 | A 10-6 | B 10-1 | B 10-2 |
| Measurement 1 | 0.2276 | −0.5481 | −0.2021 | −0.2030 | −0.5479 | 0.1773 | 0.2088 | −0.5474 |
| Measurement 2 | 0.2299 | −0.5454 | −0.1991 | −0.1979 | −0.5354 | 0.2096 | 0.2363 | −0.5417 |
| Measurement 3 | 0.2384 | −0.5471 | −0.2095 | −0.1966 | −0.5479 | 0.1811 | 0.2148 | −0.5524 |
| Measurement 4 | 0.2468 | −0.5573 | −0.1982 | −0.1939 | −0.5434 | 0.1932 | 0.2113 | −0.5548 |
| Variance: | 7.618E-05 | 2.866E-05 | 2.629E-05 | 1.467E-05 | 3.466E-05 | 2.119E-03 | 1.584E-04 | 3.377E-05 |
| Mean: | 0.2357 | −0.5495 | −0.2022 | −0.1978 | −0.5437 | 0.1903 | 0.2178 | −0.5491 |

| | B 10-3 | B 10-4 | B 10-5 | B 10-6 | C 10-1 | C 10-2 | C 10-3 | C 10-4 |
|---|---|---|---|---|---|---|---|---|
| Measurement 1 | −0.2395 | −0.2079 | −0.5699 | 0.1670 | 0.2480 | −0.5471 | −0.1908 | −0.1828 |
| Measurement 2 | −0.2116 | −0.2309 | −0.5627 | 0.2337 | 0.2683 | −0.5383 | −0.1899 | −0.1886 |
| Measurement 3 | −0.2424 | −0.2381 | −0.5637 | 0.1677 | 0.2759 | −0.5330 | −0.1883 | −0.1862 |
| Measurement 4 | −0.2312 | −0.2292 | −0.5769 | 0.1810 | 0.2501 | −0.5356 | −0.1911 | −0.1756 |
| Variance: | 1.936E-04 | 1.689E-04 | 4.32E-05 | 9.967E-04 | 1.876E-04 | 3.765E-05 | 1.506E-06 | 3.184E-05 |
| Mean: | −0.2312 | −0.2265 | −0.5683 | 0.1874 | 0.2606 | −0.5385 | −0.1900 | −0.1833 |

| | C 10-5 | C 10-6 | D 10-1 | D 10-2 | D 10-2 | D 10-4 | D 10-5 | D 10-6 |
|---|---|---|---|---|---|---|---|---|
| Measurement 1 | −0.5449 | 0.2154 | 0.2435 | −0.5597 | −0.2321 | −0.2200 | −0.5633 | 0.1974 |
| Measurement 2 | −0.5615 | 0.2234 | 0.2609 | −0.5486 | −0.2191 | −0.2104 | −0.5626 | 0.2431 |
| Measurement 3 | −0.5488 | 0.2247 | 0.2687 | −0.5496 | −0.1994 | −0.1999 | −0.5552 | 0.2597 |
| Measurement 4 | −0.5453 | 0.2428 | 0.2861 | −0.5452 | −0.2055 | −0.1891 | −0.5466 | 0.2766 |
| Variance: | 6.044E-05 | 1.341E-04 | 3.124E-04 | 3.882E-05 | 2.134E-04 | 1.776E-04 | 6.078E-05 | 1.161E-03 |
| Mean: | −0.5501 | 0.2266 | 0.2648 | −0.5508 | −0.2141 | −0.2048 | −0.5570 | 0.2442 |
| | MSE = 0.0001835 | | OMEGA = 0.0354918 | | | | | |

TABLE 4

Fingerprint Data

| | A 10-1 | A 10-2 | A 10-3 | A 10-4 | A 10-5 | A 10-6 | B 10-1 | B 10-2 | B 10-3 | B 10-4 | B 10-5 | B 10-6 | C 10-1 | C 10-2 | C 10-3 | C 10-4 | C 10-5 | C 10-6 | D 10-1 | D 10-2 | D 10-3 | D 10-4 | D 10-5 | D 10-6 |
|---|---|---|---|---|---|---|---|---|---|---|---|---|---|---|---|---|---|---|---|---|---|---|---|---|
| A 10-1 | 0 | 1 | 1 | 1 | 1 | 1 | 0 | 1 | 1 | 1 | 1 | 1 | 0 | 1 | 1 | 1 | 1 | 0 | 0 | 1 | 1 | 1 | 1 | 0 |
| A 10-2 | 1 | 0 | 1 | 1 | 0 | 1 | 1 | 0 | 1 | 1 | 0 | 1 | 1 | 0 | 1 | 1 | 0 | 1 | 1 | 0 | 1 | 1 | 0 | 1 |
| A 10-3 | 1 | 1 | 0 | 0 | 1 | 1 | 1 | 1 | 0 | 0 | 1 | 1 | 1 | 1 | 0 | 0 | 1 | 1 | 1 | 1 | 0 | 0 | 1 | 1 |
| A 10-4 | 1 | 1 | 0 | 0 | 1 | 1 | 1 | 1 | 0 | 0 | 1 | 1 | 1 | 1 | 0 | 0 | 1 | 1 | 1 | 1 | 0 | 0 | 1 | 1 |
| A 10-5 | 1 | 0 | 1 | 1 | 0 | 1 | 1 | 0 | 1 | 1 | 0 | 1 | 1 | 0 | 1 | 1 | 0 | 1 | 1 | 0 | 1 | 1 | 0 | 1 |
| A 10-6 | 1 | 1 | 1 | 1 | 1 | 0 | 0 | 1 | 1 | 1 | 1 | 0 | 1 | 1 | 1 | 1 | 1 | 1 | 1 | 1 | 1 | 1 | 1 | 1 |
| B 10-1 | 0 | 1 | 1 | 1 | 1 | 0 | 0 | 1 | 1 | 1 | 1 | 0 | 1 | 1 | 1 | 1 | 1 | 0 | 1 | 1 | 1 | 1 | 1 | 0 |
| B 10-2 | 1 | 0 | 1 | 1 | 0 | 1 | 1 | 0 | 1 | 1 | 0 | 1 | 1 | 0 | 1 | 1 | 0 | 1 | 1 | 0 | 1 | 1 | 0 | 1 |
| B 10-3 | 1 | 1 | 0 | 0 | 1 | 1 | 1 | 1 | 0 | 0 | 1 | 1 | 1 | 1 | 1 | 1 | 1 | 1 | 1 | 1 | 0 | 0 | 1 | 1 |
| B 10-4 | 1 | 1 | 0 | 0 | 1 | 1 | 1 | 1 | 0 | 0 | 1 | 1 | 1 | 1 | 1 | 1 | 1 | 1 | 1 | 1 | 0 | 0 | 1 | 1 |
| B 10-5 | 1 | 0 | 1 | 1 | 0 | 1 | 1 | 0 | 1 | 1 | 0 | 1 | 1 | 0 | 1 | 1 | 0 | 1 | 1 | 0 | 1 | 1 | 0 | 1 |
| B 10-6 | 1 | 1 | 1 | 1 | 1 | 0 | 0 | 1 | 1 | 1 | 1 | 0 | 1 | 1 | 1 | 1 | 1 | 1 | 1 | 1 | 1 | 1 | 1 | 1 |
| C 10-1 | 0 | 1 | 1 | 1 | 1 | 1 | 1 | 1 | 1 | 1 | 1 | 1 | 0 | 1 | 1 | 1 | 1 | 0 | 0 | 1 | 1 | 1 | 1 | 0 |
| C 10-2 | 1 | 0 | 1 | 1 | 0 | 1 | 1 | 0 | 1 | 1 | 0 | 1 | 1 | 0 | 1 | 1 | 0 | 1 | 1 | 0 | 1 | 1 | 0 | 1 |
| C 10-3 | 1 | 1 | 0 | 0 | 1 | 1 | 1 | 1 | 1 | 1 | 1 | 1 | 1 | 1 | 0 | 0 | 1 | 1 | 1 | 1 | 0 | 0 | 1 | 1 |
| C 10-4 | 1 | 1 | 0 | 0 | 1 | 1 | 1 | 1 | 1 | 1 | 1 | 1 | 1 | 1 | 0 | 0 | 1 | 1 | 1 | 1 | 0 | 0 | 1 | 1 |
| C 10-5 | 1 | 0 | 1 | 1 | 0 | 1 | 1 | 0 | 1 | 1 | 0 | 1 | 1 | 0 | 1 | 1 | 0 | 1 | 1 | 0 | 1 | 1 | 0 | 1 |
| C 10-6 | 0 | 1 | 1 | 1 | 1 | 1 | 0 | 1 | 1 | 1 | 1 | 1 | 0 | 1 | 1 | 1 | 1 | 0 | 1 | 1 | 1 | 1 | 1 | 0 |
| D 10-1 | 0 | 1 | 1 | 1 | 1 | 1 | 1 | 1 | 1 | 1 | 1 | 1 | 0 | 1 | 1 | 1 | 1 | 1 | 0 | 1 | 1 | 1 | 1 | 0 |
| D 10-2 | 1 | 0 | 1 | 1 | 0 | 1 | 1 | 0 | 1 | 1 | 0 | 1 | 1 | 0 | 1 | 1 | 0 | 1 | 1 | 0 | 1 | 1 | 0 | 1 |
| D 10-3 | 1 | 1 | 0 | 0 | 1 | 1 | 1 | 1 | 0 | 0 | 1 | 1 | 1 | 1 | 0 | 0 | 1 | 1 | 1 | 1 | 0 | 0 | 1 | 1 |
| D 10-4 | 1 | 1 | 0 | 0 | 1 | 1 | 1 | 1 | 0 | 0 | 1 | 1 | 1 | 1 | 0 | 0 | 1 | 1 | 1 | 1 | 0 | 0 | 1 | 1 |
| D 10-5 | 1 | 0 | 1 | 1 | 0 | 1 | 1 | 0 | 1 | 1 | 0 | 1 | 1 | 0 | 1 | 1 | 0 | 1 | 1 | 0 | 1 | 1 | 0 | 1 |
| D 10-6 | 0 | 1 | 1 | 1 | 1 | 1 | 0 | 1 | 1 | 1 | 1 | 1 | 0 | 1 | 1 | 1 | 1 | 0 | 0 | 1 | 1 | 1 | 1 | 0 |

(rfu). The emission measurements are always made in the region of linear response, which on this fluorescence measuring instrument is made between 200 and 2000 rfu.

Each working solution (150 µL) was added to the test plate using an automated handling device with less than 5% error in volume measurement. The working solution/plate combination was measured for background fluorescence to account for variability in composition, plate dimensions, and laser output. Excitation and emission experiments can be run on any laser or non-laser fluorescence detection system. In this set of experiments the measurements were made using a FluorImager 575 (Molecular Dynamics, Sunnyvale, Calif.).

The neutral spirits samples were added directly to the sample plate. A key discovery in analyzing neutral spirits (96% ethanol) is that the analysis of the residual water is important. The signal from Compound 3 is designed to analyze the residual water. However, the high concentrations of ethanol in the samples masks the signal from the water. For this identification method to work well, the ethanol is removed under vacuum from the samples after they have been added to the individual microwells of the plate. This reduction allows the exact analysis of the water in the neutral spirits samples. Since the reduction takes place directly on the microwell plates, all samples are treated equally and the process is automated by placing a vacuum bell on the automated plate-handling work station.

The results of the experiment are presented in Table 3. Variance and mean were calculated for each group (A, B, C, or D) of 4 measurements. The 95% confidence levels were used for this fingerprint analysis. If two sample means differ by an amount greater than the omega, the samples are different (i.e., substantially different in composition). For example, in test A, sample 10-1 had a mean light emission intensity of 0.2357 and sample 10-2 had a mean light emission intensity of −0.5495. The difference in light emission intensity was 0.7852. The omega for test A was 0.0354918. If the difference (0.7852) is greater than omega (0.0354918) for any two samples, then the samples are different. Therefore, 10-1 and 10-2 are different. The comparison is made based strictly on the statistical data and can be done automatically, without the need for further interpretation.

The fingerprint data are presented in Table 4 to make all possible comparisons. A value of 1 in Table 4 indicates that the two sample means differ by more than omega. The value of 0 indicates that two samples do not differ by more than omega. Thus, a value of 0 signifies that the samples are pairs (i.e., substantially similar in composition, such as different batches or lots) or that the sample tested against itself (along the upper left-to-lower right diagonal of Table 4) and a value of 1 signifies that the samples are different. When sample pairs are consistently different, the samples are determined to have substantially different compositions (i.e., different brands altogether).

As a result of the fingerprinting analysis in Table 4, products 10-1 and 10-6, 10-2 and 10-5, and 10-3 and 10-4 were determined to be pairs (i.e., substantially similar in composition) that are different from each other (i.e., different lots).

EXAMPLE 2-DISTILLED SPIRITS

In a manner similar to that described in Example 1, it is possible to authenticate distilled spirits, such as vodka. For this fingerprint analysis, Compound 1, Compound 2, Compound 3, Compound 4, Compound 5, Compound 6, Compound 7, and Compound 8 can be used.

The stock solution of Compound 1 was 1.5 mM in a 1:1 DMSO/water mixture. The stock solution of Compound 2 was 2 mM in DMSO. The stock solution of Compound 3 was 0.5 mM in a 1:1 DMSO/water mixture. The stock solution of Compound 4 was 1 mM in DMSO. The stock solution of Compound 5 was 1 mM in distilled water. The stock solution of Compound 6 was 1 mM in DMSO. The stock solution of Compound 7 was 1 mm in distilled water. The stock solution of Compound 8 was 4 mg/mL in ethanol (chromatography grade, Sigma Chemical Company, St. Louis, Mo.).

Working solution concentrations were determined as in Example 1. The optimum concentration of light-emissive compound was determined to be the level that allows discrimination of known samples having value differences greater than omega. The working solution of Compound 2 was prepared by diluting 120 µL of the 2mM stock solution in 20 mL of distilled water. The working solution of Compound 3 was prepared by diluting 100 µL of the stock solution in 20 mL of distilled water. The working solution of Compound 4 was prepared by diluting 100 µL of the stock solution in 50 mL of distilled water. The working solution of Compound 5 was prepared by diluting 75 µL of the stock solution in 50 mL of distilled water. The working solution of Compound 6 was prepared by diluting 50 µL of the stock solution in 50 mL of ethanol. The working solution of Compound 7 was prepared by diluting 25 µL of the stock solution in 50 mL of distilled water. The working solution of Compound 8 was prepared by diluting 50 µL of the stock solution in 50 mL of distilled water.

Compounds 1, 2, 3, 4, 5, 6, and 8 require a 530BP±15 nm band pass filter to reduce the excitation wavelength intensity during emission measurements. Compound 7 requires the use of a 515 nm Long Pass filter (LP).

Each working solution (150 µL) was added to the test plate using an automated handling device with less than 5% error in volume measurement as in Example 1. The distilled spirits (vodka) samples were analyzed as described in Example 1.

EXAMPLE 3-CARBONATED DRINKS AND FRUIT BEVERAGES

The analysis methods of the invention can be used in the soft drink and fruit juice industry, particularly to check third party re-formulations in every lot to monitor licensing agreements, for example. The analysis speed needed to check samples of this type should be faster than 300 samples/hour. This was not a double blind test.

Product formulations can be verified by methods similar to those described in Example 1. The fingerprint is the same when the product is produced to the same high quality of standards. Referring to Table 5, light emission was monitored in an array of six samples (Pepsi 1, Pepsi 2, Diet Pepsi 3, Coke Classic 4, Diet Coke 5, and Black Cherry 6) that were each tested four times with the four different light-emissive compounds (A, B, C, and D). Test A used Compound 1. Test B used Compound 2. Test C used Compound 3. Test D used Compound 9. Each sample of the product was tested four times with each light-emissive compound.

The test methods were generally conducted in the following manner. The beverages or juices were diluted 1:10 to 1:300 with water for optimum reaction with the light-emissive compounds. The optimum response of the sample is determined empirically, by using a concentration curve to maximize emission response. The sample concentration was selected to give one-half of the maximum emission response with the tested sample.

TABLE 5

| STATISTICAL DATA | | | | | | HFCS/sucrose liquid | |
|---|---|---|---|---|---|---|---|
| A Pepsi 1 | A Pepsi 2 | A Diet Pepsi | A Coke Classic | A Diet Coke | A Black Cherry | B Pepsi 1 | B Pepsi 2 |

TABLE 5-continued

|   | | | | | | | | |
|---|---|---|---|---|---|---|---|---|
| Measurement 1 | −0.8311 | −0.8360 | −0.7252 | −0.8701 | −0.6664 | −0.8449 | −0.3578 | −0.3040 |
| Measurement 2 | −0.8473 | −0.8358 | −0.7179 | −0.8716 | −0.6614 | −0.8368 | −0.3471 | −0.3294 |
| Measurement 3 | −0.8315 | −0.8349 | −0.7157 | −0.8721 | −0.6414 | −0.8432 | −0.3254 | −0.3186 |
| Measurement 4 | −0.8407 | −0.8293 | −0.7145 | −0.8633 | −0.6544 | −0.8368 | −0.3368 | −0.2848 |
| Variance: | 6.105E-05 | 9.985E-06 | 2.301E-05 | 1.644E-05 | 1.179E-04 | 1.795E-05 | 1.924E-04 | 3.725E-04 |
| Mean: | −0.8376 | −0.8340 | −0.7183 | −0.8693 | −0.6559 | −0.8404 | −0.3418 | −0.3092 |

|   | B Diet Pepsi | B Coke Classic | B Diet Coke | B Black Cherry | C Pepsi 1 | C Pepsi 2 | C Diet Pepsi | C Coke Classic |
|---|---|---|---|---|---|---|---|---|
| Measurement 1 | 0.3592 | −0.2481 | 0.7057 | −0.6725 | 2.3477 | 2.4311 | 3.2869 | 2.2283 |
| Measurement 2 | 0.3953 | −0.2200 | 0.7018 | −0.6583 | 2.4218 | 2.2661 | 3.2057 | 2.2739 |
| Measurement 3 | 0.3907 | −0.2192 | 0.7283 | −0.6620 | 2.4042 | 2.4579 | 3.2358 | 2.3609 |
| Measurement 4 | 0.4028 | −0.2119 | 0.7634 | −0.6731 | 2.4532 | 2.5020 | 3.3130 | 2.4228 |
| Variance: | 3.886E-04 | 2.551E-02 | 7.983E-04 | 5.589E-05 | 1.958E-03 | 1.061E-02 | 2.357E-05 | 7.589E-03 |
| Mean: | 0.3870 | −0.2248 | 0.7248 | −0.6665 | 2.4067 | 2.4143 | 3.2603 | 2.3215 |

|   | C Diet Coke | C Black Cherry | D Pepsi 1 | D Pepsi 2 | D Diet Pepsi | D Coke Classic | D Diet Coke | D Black Cherry |
|---|---|---|---|---|---|---|---|---|
| Measurement 1 | 3.4794 | 1.6844 | 8.6589 | 8.8383 | 7.3358 | 8.0844 | 6.8748 | 10.4029 |
| Measurement 2 | 3.4689 | 1.6986 | 8.7641 | 9.1611 | 7.3981 | 8.3034 | 6.9779 | 10.5467 |
| Measurement 3 | 3.5929 | 1.7489 | 9.1029 | 9.1162 | 7.5821 | 8.2324 | 7.0303 | 10.5861 |
| Measurement 4 | 3.6457 | 1.9201 | 9.4517 | 9.3065 | 7.5014 | 8.6027 | 7.1879 | 11.0469 |
| Variance: | 7.507E-03 | 1.174E-02 | 0.1288 | 3.833E-02 | 1.192E-02 | 4.752E-02 | 1.705E-02 | 7.776E-02 |
| Mean: | 3.5467 | 1.7630 | 8.9944 | 9.1055 | 7.4544 | 8.3057 | 7.0177 | 10.6456 |
| | MSE = 0.0152267 | | OMEGA = 0.3232988 | | | | | |

TABLE 6

|   | Fingerprint Data | | | | | | | | | | | HFCS/Sucrose Liquids | | | | | | | | | | | |
|---|---|---|---|---|---|---|---|---|---|---|---|---|---|---|---|---|---|---|---|---|---|---|---|
|   | A Pepsi 1 | A Pepsi 2 | A Diet Pepsi | A Coke | A Diet Coke | A Blk Che | B Pepsi 1 | B Pepsi 2 | B Diet Pepsi | B Coke | B Diet Coke | B Blk Che | C Pepsi 1 | C Pepsi 2 | C Diet Pepsi | C Coke | C Diet Coke | C Blk Che | D Pepsi 1 | D Pepsi 2 | D Diet Pepsi | D Coke | D Diet Coke | D Blk Che |
| A Pepsi 1 | 0 | 0 | 0 | 0 | 0 | 0 | 1 | 1 | 1 | 1 | 1 | 0 | 1 | 1 | 1 | 1 | 1 | 1 | 1 | 1 | 1 | 1 | 1 | 1 |
| A Pepsi 2 | 0 | 0 | 0 | 0 | 0 | 0 | 1 | 1 | 1 | 1 | 1 | 0 | 1 | 1 | 1 | 1 | 1 | 1 | 1 | 1 | 1 | 1 | 1 | 1 |
| A Diet Pepsi | 0 | 0 | 0 | 0 | 0 | 0 | 1 | 1 | 1 | 1 | 1 | 0 | 1 | 1 | 1 | 1 | 1 | 1 | 1 | 1 | 1 | 1 | 1 | 1 |
| A Coke | 0 | 0 | 0 | 0 | 0 | 0 | 1 | 1 | 1 | 1 | 1 | 0 | 1 | 1 | 1 | 1 | 1 | 1 | 1 | 1 | 1 | 1 | 1 | 1 |
| A Diet Coke | 0 | 0 | 0 | 0 | 0 | 0 | 0 | 1 | 1 | 1 | 1 | 0 | 1 | 1 | 1 | 1 | 1 | 1 | 1 | 1 | 1 | 1 | 1 | 1 |
| A Blk Che | 0 | 0 | 0 | 0 | 0 | 0 | 1 | 1 | 1 | 1 | 1 | 0 | 1 | 1 | 1 | 1 | 1 | 1 | 1 | 1 | 1 | 1 | 1 | 1 |
| B Pepsi 1 | 1 | 1 | 1 | 1 | 1 | 1 | 0 | 0 | 1 | 1 | 1 | 1 | 1 | 1 | 1 | 1 | 1 | 1 | 1 | 1 | 1 | 1 | 1 | 1 |
| B Pepsi 2 | 1 | 1 | 1 | 1 | 1 | 1 | 0 | 0 | 1 | 1 | 1 | 1 | 1 | 1 | 1 | 1 | 1 | 1 | 1 | 1 | 1 | 1 | 1 | 1 |
| B Diet Pepsi | 1 | 1 | 1 | 1 | 1 | 1 | 1 | 1 | 0 | 1 | 1 | 1 | 1 | 1 | 1 | 1 | 1 | 1 | 1 | 1 | 1 | 1 | 1 | 1 |
| B Coke | 1 | 1 | 1 | 1 | 1 | 1 | 0 | 0 | 1 | 0 | 1 | 1 | 1 | 1 | 1 | 1 | 1 | 1 | 1 | 1 | 1 | 1 | 1 | 1 |
| B Diet Coke | 1 | 1 | 1 | 1 | 1 | 1 | 1 | 1 | 1 | 1 | 0 | 1 | 1 | 1 | 1 | 1 | 1 | 1 | 1 | 1 | 1 | 1 | 1 | 1 |
| B Blk Che | 0 | 0 | 0 | 0 | 0 | 0 | 1 | 1 | 1 | 1 | 1 | 0 | 1 | 1 | 1 | 1 | 1 | 1 | 1 | 1 | 1 | 1 | 1 | 1 |
| C Pepsi 1 | 1 | 1 | 1 | 1 | 1 | 1 | 1 | 1 | 1 | 1 | 1 | 1 | 0 | 0 | 1 | 0 | 1 | 1 | 1 | 1 | 1 | 1 | 1 | 1 |
| C Pepsi 2 | 1 | 1 | 1 | 1 | 1 | 1 | 1 | 1 | 1 | 1 | 1 | 1 | 0 | 0 | 1 | 0 | 1 | 1 | 1 | 1 | 1 | 1 | 1 | 1 |
| C Diet Pepsi | 1 | 1 | 1 | 1 | 1 | 1 | 1 | 1 | 1 | 1 | 1 | 1 | 1 | 1 | 0 | 1 | 0 | 1 | 1 | 1 | 1 | 1 | 1 | 1 |
| C Coke | 1 | 1 | 1 | 1 | 1 | 1 | 1 | 1 | 1 | 1 | 1 | 1 | 0 | 0 | 1 | 0 | 1 | 1 | 1 | 1 | 1 | 1 | 1 | 1 |
| C Diet Coke | 1 | 1 | 1 | 1 | 1 | 1 | 1 | 1 | 1 | 1 | 1 | 1 | 1 | 1 | 0 | 1 | 0 | 1 | 1 | 1 | 1 | 1 | 1 | 1 |
| C Blk Che | 1 | 1 | 1 | 1 | 1 | 1 | 1 | 1 | 1 | 1 | 1 | 1 | 1 | 1 | 1 | 1 | 0 | 1 | 1 | 1 | 1 | 1 | 1 | 1 |
| D Pepsi 1 | 1 | 1 | 1 | 1 | 1 | 1 | 1 | 1 | 1 | 1 | 1 | 1 | 1 | 1 | 1 | 1 | 1 | 1 | 0 | 0 | 1 | 1 | 1 | 1 |
| D Pepsi 2 | 1 | 1 | 1 | 1 | 1 | 1 | 1 | 1 | 1 | 1 | 1 | 1 | 1 | 1 | 1 | 1 | 1 | 1 | 0 | 0 | 1 | 1 | 1 | 1 |
| D Diet Pepsi | 1 | 1 | 1 | 1 | 1 | 1 | 1 | 1 | 1 | 1 | 1 | 1 | 1 | 1 | 1 | 1 | 1 | 1 | 1 | 1 | 0 | 1 | 1 | 1 |
| D Coke | 1 | 1 | 1 | 1 | 1 | 1 | 1 | 1 | 1 | 1 | 1 | 1 | 1 | 1 | 1 | 1 | 1 | 1 | 1 | 1 | 1 | 0 | 1 | 1 |
| D Diet Coke | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 0 | 1 |
| D Blk Che | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 0 |

Stock solutions of the light-emissive compounds were prepared by dissolving Compound 1 at a concentration of 1.5 mM in 1:2 DMSO/water, Compound 2 at a concentration of 2 mM in DMSO, Compound 3 at a concentration of 1 mM in DMSO, and Compound 9 at a concentration of 10 mM in DMSO.

The concentrations of working solutions of light emissive compounds were optimized as described in Example 1. Optimum concentrations were calculated from the concentrations of light-emissive compound that provide emission intensity values that can discriminate a standard product sample from other the unknown samples by a value greater than omega. The working solution of Compound 1 was prepared by diluting 75 µL of the stock solution in 50 mL of distilled water. The working solution of Compound 2 was prepared by diluting 120 µL of the stock solution in 20 mL of distilled water. The working solution of Compound 3 was prepared by diluting 100 µL of the stock solution in 20 mL of distilled water. The working solution of Compound 9 was prepared by diluting 50 µL of the stock solution in 50 mL of distilled water.

Compounds 1, 2, 3, and 9 require a 530BP±15 nm band pass filter to reduce the excitation wavelength intensity during the emission measurements. The sample placement and emission analysis was carried out as described in Example 1.

The results of the experiment are presented in Table 5. There were four different measurements (A, B, C, and D) made for each sample in combination with each light-emissive compound. Each measurement was repeated four times to demonstrate the level of reproducibility. Variance and mean were calculated for each group of 4 measurements. The 95% confidence levels were used for this fingerprint analysis. If two sample means differ by an amount greater than omega, the samples are different (i.e., substantially similar in composition).

For example, in the test with light-emissive compound D, sample Pepsi 1 had a mean light emission of 8.9944 and sample Pepsi 2 had a mean light emission of 9.1055. The difference in light emission was 0.1111. The omega for the test was 0.3232988. If the difference (0.1111) is greater than omega for any two samples, then the samples are substantially the same. Therefore, Pepsi 1 and Pepsi 2 are substantially the same.

The fingerprint data are presented in Table 6 to make all possible comparisons and are established in the same manner as in Example 1. As a result of the fingerprinting analysis in Table 6, Pepsi 1 and Pepsi 2 are pairs, with similar compositions, and the other samples are not related.

EXAMPLE 4-ONE-STEP ANALYSIS OF BEVERAGES

The methods of Example 3 can be modified to monitor key ingredients in beverages. Importantly, it was discovered that the key ingredients that are currently measured by standard analytical methods for authenticity monitoring can also be measured by the methods of automated emission measurements of the invention. In other words, there are some ingredients inherent to certain products that have characteristic light-emission properties. The methods can be used to analyze these components in a single-plate analysis with the all the light-emissive compounds combined together, thereby allowing modification and automation of the method into a simple, one-step inexpensive emission scan.

Standard ingredients that are monitored in colas are, for example, high fructose corn syrup (HFCS), caffeine, potassium benzoate, sodium benzoate, pH, and aspartame. Two combinations of light-emissive compounds have been developed for the analysis of colas. Combination 1 allows monitoring of sugar (or HFCS) sources, caffeine, pH, and preservatives (such as potassium or sodium benzoate). Combination 1 is useful for analyzing ordinary carbonated beverages. Combination 2 is tailored for the analysis of diet carbonated beverages and allows monitoring of aspartame, caffeine, pH, and preservatives. The Combinations are designed to detect changes in specific ingredients from at 0.1, 0.3, 0.5, 1, 2, and 3 percent reduction levels.

Combination 1 includes Compound 1, Compound 3, and Compound 11 for the analysis of sugar (or HFCS). Caffeine is a light-emissive compound alone and does not require addition of another component to the mixture. The common preservatives, potassium and sodium benzoate, can be identified using a number of light-emissive compounds. For example, Compound 12 is a potassium sensitive dye. The carboxylic acid on the benzoate group is reactive with all alkyl halide, carbodimide, and alcohol containing light-emissive compounds (see Table 1). The pH can be determined using any pH-sensitive light-emissive compound that emits in range from of pH from 1-4 (most soft drinks range in pH from 2.4–4.0). A specific example of a pH-sensitive light-emissive compound is Compound 13.

Stock solutions of the light-emissive compounds were prepared by dissolving Compound 1 at a concentration of 1.5 mM in a 1:1 DMSO/water mixture, Compound 3 at a concentration of 0.5 mM in 1:1 mixture of DMSO/water, Compound 11 at a concentration of 10 mM in ethanol, Compound 12 at a concentration of 10 mM in DMSO, and Compound 13 at a concentration of 10 mM in distilled water.

The working concentrations were optimized for identification of key ingredients for each soft drink beverage product, as described in Example 1. The working solution of Compound 1 was prepared by diluting 75 µL of the stock solution in 50 mL of distilled water. The working solution of Compound 3 was prepared by diluting 100 µL of the stock solution in 20 mL of water. The working solution of Compound 11 was prepared by diluting 50 µL of the stock solution in 50 mL of distilled water. The working solution of Compound 12 was prepared by diluting 50 µL of the stock solution in 50 mL of distilled water. The working solution of Compound 13 was prepared by diluting 50 µL in 100 mL of distilled water.

Caffeine (anhydrous; Sigma Reference Standard Product #C-1778) was used as a standard in a caffeine-free beverage (product specific) as an internal calibration standard for the presence of caffeine. Caffeine has excitation maxima at 254 nm and 330 nm and an emission maximum at 350 nm.

Compound 1 and Compound 3 both require a 520BP±15 nm band pass filter. Caffeine requires a 345LP nm long pass filter. Compound 11 requires a 365BP±15 band pass filter. Compound 12 requires a 460BP±6.8 nm band pass filter. Compound 13 requires a 550BP±15 nm band pass filter.

Combination 2, for analyzing diet carbonated beverages is essentially the same as Combination 1 except that Compounds 1, 3, and 11 are replaced by light-emissive compounds that indicate the relative presence of aspartame. These include light-emissive compounds that react, or interact, with carboxylic acid groups and amine groups. See Table 1 for examples.

EXAMPLE 5-INFANT FORMULAS

The methods of the invention can be used in the infant formula industry as for product authentication. In 1995, a counterfeit-labeled version of infant formula was illegally distributed to grocery chains in 16 states. Authenticating infant formula on shelves can help assure formula customers that a product is authentic and reliable. Using the methods, one can insure that the product at the source matches the product at the destination. In addition, it can be possible to detect product tampering by fingerprint analysis.

Product formulations can be verified by methods similar to those described in Example 1. The fingerprint is the same when the product is produced to the same high quality of standards. Referring to Table 7, light emission was monitored in an array of six samples (Gerber, Similac liquid, Similac powder, Carnation Follow-Up, Enfamil, and a powdered milk standard) that were each tested four times with a light-emissive compound. The light-emissive compound included Compound 1, Compound 2, Compound 3, and Compound 7.

The samples were prepared by diluting the infant formulas with distilled water according to manufacturer instructions (e.g., 8.5 grams in 60 mL of distilled water). The resulting solutions were further diluted by a factor of 1000, and filtered using a Millipore 0.22 μm sterile syringe filter. The filter samples were used directly in the analyses.

ner as in Example 1. As a result of the fingerprinting analysis in Table 8, the Gerber, Similac and Enfamil samples are the same. However, the Carnation and Standard are different. The Standard is Carnation Evaporated Milk.

TABLE 7

|  | Gerber | Similac Lq | Similac | PwCarnation | Enfamil | Standard |
|---|---|---|---|---|---|---|
| Meas. 1 | −0.2022 | −0.1912 | −0.2109 | −0.3088 | −0.2143 | −0.1022 |
| Meas. 2 | −0.2025 | −0.2061 | −0.2102 | −0.3196 | −0.1511 | −0.1154 |
| Meas. 3 | −0.1988 | −0.1814 | −0.2410 | −0.3037 | −0.2493 | −0.1094 |
| Meas. 4 | −0.2159 | −0.1979 | −0.1926 | −0.3162 | −0.2005 | −0.1155 |
| Variance: | 5.708E-05 | 0.0001094 | 0.0004035 | 5.163E-05 | 0.0016566 | 3.968E-05 |
| Mean: | −0.2049 | −0.1942 | −0.2137 | −0.3121 | −0.2038 | −0.1106 |
| MSE = 0.0195 |  | OMEGA = 0.044 |  |  |  |  |

TABLE 8

|  | Gerber | Similar Lq | Similar | Pw Carnation | Enfamil | Standard |
|---|---|---|---|---|---|---|
| Gerber | 0 | 0 | 0 | 1 | 0 | 1 |
| Similac Lq | 0 | 0 | 0 | 1 | 0 | 1 |
| Similac Pw | 0 | 0 | 0 | 1 | 0 | 1 |
| Carnation | 1 | 1 | 1 | 0 | 1 | 0 |
| Enfamil | 0 | 0 | 0 | 1 | 0 | 1 |
| Standard | 1 | 1 | 1 | 0 | 1 | 0 |

Stock solutions of the light-emissive compounds were prepared that contained Compound 1 at a concentration of 1.5 mM in a 1:2 DMSO/water mixture, Compound 2 at a concentration of 2 mM in DMSO, Compound 3 at a concentration of 1 mM in DMSO, and Compound 7 at a concentration of 1 mM in distilled water.

Working solution concentrations were determined as described in Example 1. The working solution of Compound 1 was prepared by diluting 75 μL of the stock solution in 20 mL of distilled water. The working solution of Compound 2 was prepared by diluting 120 μL of the stock solution in 20 mL of distilled water. The working solution of Compound 3 was prepared by diluting 100 μL of the stock solution in 20 mL of distilled water. The working solution of Compound 7 was prepared by diluting 25 μL of the stock solution in 50 mL of distilled water.

Compounds 1, 2, 3, and 7 require a 530BP±15 nm band pass filter to reduce the excitation wavelength intensity in the emission measurement. The analysis was conducted as described in Example 1. The diluted and filtered samples were added directly to the dyes and the emission measured.

The results of the experiment are presented in Table 7. There was one measurements made for each sample in combination with the light-emissive compound. Each measurement was repeated four times to demonstrate the level of reproducibility. Variance and mean were calculated for each group of 4 measurements. The 95% confidence levels were used for this fingerprint analysis. The analysis is similar to that described in Examples 1 and 2.

For example, the Gerber sample had a mean light emission of −0.2049 and the Similac sample had a mean light emission of −0.1941. The difference in light emission was 0.0108. The omega for the test was 0.044. If the difference (0.0108) is less than omega for any two samples, then the samples are substantially the same. Therefore, the products are substantially the same.

The fingerprint data are presented in Table 8 to make all possible comparisons and are established in the same man- Other embodiments are within the claims.

What is claimed is:

1. A method for determining relatedness of a sample to a standard know to be authentic or known to have at least one selected characteristic of authentic material, the method comprising:

a. combining a sample with at least one light-emissive compound to form a sample mixture;

b. irradiating the sample mixture with an irradiating wavelength of light;

c. monitoring at least one emitted wavelength of light, generated by the sample mixture in response to the irradiating wavelength of light, to establish a sample fingerprint;

d. providing a standard fingerprint characteristic of a standard mixture, the standard mixture comprising the standard and the light-emissive compound and the standard fingerprint being generated by irradiating the standard mixture with the irradiating wavelength of light and monitoring the at least one emitted wavelength of light, generated by the standard mixture, in response thereto, wherein the light-emissive compound is selected so as to interact with the standard to provide a characteristic light emission; and e. comparing the sample fingerprint with the standard fingerprint to determine whether the sample is authentic.

2. The method of claim 1 in which the light-emissive compound is added to the sample by an automated pipette.

3. The method of claim 1, wherein the sample mixture is dispensed by an automated pipette in a multiwell plate.

4. The method of claim 1 in which the light-emissive compound is fluorescent, phosphorescent, or luminescent.

5. The method of claim 1 in which the light-emissive compound reacts with components of the sample or the standard or both to yield at least one fluorescent, phosphorescent, or luminescent component.

6. The method of claim 1 in which steps (b)–(c) are repeated at least three times using the same light-emissive emissive compounds and the same irradiating and emission wavelengths to establish a fingerprint emission profile for the sample.

7. The method of claim 1, in which the standard is a caffeine-containing beverage, and the light-emissive compound is selected from the group consisting of 5-(2-carbohydrazinomethylthioacetyl)aminofluorescein, 5-(4,6-dichlorotriazinyl)aminofluorescein, Fluo-3 pentaammonium salt, 4-aminofluorescein, 5-aminofluorescein, sulfite blue coumarin, courmarin diacid cryptand (CD222), and Eosin Y.

8. The method of claim 1, in which the standard is an infant formula, and the light-emissive compound is selected from the group consisting of 5-(2-carbohydrazinomethylthioacetyl)aminofluorescein, 5-(4,6-dichlorotriazinyl)aminofluorescein, Fluo-3 pentaammonium salt, and BTC-5N.

9. The method of claim 1, in which the standard contains corn syrup, and the light-emissive compound is selected from the group consisting of 5-(2-carbohydrazinomethylthioacetyl)aminofluorescein, 5-(4,6-dichlorotriazinyl)aminofluorescein, Fluo-3 pentaammonium salt, 4-aminofluorescein, 5-aminofluorescein, sulfite blue coumarin, courmarin diacid cryptand (CD222), and Eosin Y.

10. The method of claim 1, in which the standard is an ethanol-containing beverage and the light-emissive compound is selected from the group consisting of 5-(2-carbohydrazinomethylthioacetyl)aminofluorescein, 5-(4,6-dichlorotriazozinyl)aminofluorescein, Fluo-3 pentaamonium salt, proflavine hemisulfate, tetra (tetramethylammonium) salt, acridine orange hydrochloride hydrate, BTC-5N, acriflavine, 4-aminofluorescein, and 5-aminofluorescien.

11. The method of claim 1, in which the standard is an aqueous mixture, and the light-emissive compound is a compound that interacts or reacts with heavy metals, the light-emissive compound being selected from the group consisting of Fluo-3 pentaammonium salt, or BTC-5N.

12. The method according to claim 1, further comprising the steps of:
providing a mixture comprising ethanol and water; and
evaporating substantially all the ethanol from the mixture to form the standard.

13. The method of claim 1, wherein the standard, the sample, or both inherently include a fluorescent, phosphorescent, or luminescent compound.

14. The method of claim 13 in which the compound is caffeine.

15. The method of claim 1 comprising performing steps (b)–(d) at least two times.

16. The method of claim 15, in which steps (b)–(c) are performed using different light-emissive compounds.

17. The method of claim 15, in which different irradiating and emission wavelengths are monitored in each performed step.

18. The method according to claim 1, further comprising the steps of:
providing a mixture comprising ethanol and water; and
evaporating substantially all the ethanol from the mixture to form the sample.

19. The method according to claim 18, further comprising the steps of:
providing a mixture comprising ethanol and water; and
evaporating substantially all the ethanol from the mixture to form the standard.

20. The method of claim 1 further comprising:
providing a background control mixture which comprises the light-emissive compound without the sample or the standard;
irradiating the background control mixture with the irradiating wavelength and monitoring the emitted wavelength in response thereto, to establish background emission; and
determining the fingerprint of the sample based on at least one difference between the emission of the control mixture and the emission of the sample mixture.

21. The method of claim 20, in which
the standard is a composition having a predetermined relative amount of a component characteristic of authentic material,
the sample fingerprint is generated based on a first change in emission, determined by comparing the background emission and the emission from the sample mixture, and the standard fingerprint is generated based on a second change in emission, determined by comparing the background emission and the standard emission, and
the comparing step comprises quantifying the relative amount of the component in the sample by comparing the first change in emission to the second change in emission.

22. The method of claim 1 or claim 20, in which
the standard is a composition having a predetermined relative amount of a component characteristic of authentic material, and
the comparing step comprises quantifying the relative amounts of the component in the sample.

23. A method for determining relatedness of a first sample to a second sample, the method comprising:
a. combining a first sample with at least one light-emissive compound to form a first sample mixture;
b. irradiating the first sample mixture with an irradiating wavelength of light;
c. monitoring at least one emitted wavelength of light generated by the first sample mixture in response to the irradiating wavelength of light, to establish a first sample mixture fingerprint characteristic of the first sample mixture;
d. providing a second sample fingerprint characteristic of a second sample mixture, the second sample mixture comprising the second sample and the light-emissive compound; and the second sample fingerprint being generated by irradiating the second sample mixture with the irradiating wavelength of light and monitoring the at least one emitted wavelength generated by the second sample mixture in response thereto wherein the light-emissive compound is as interact with the second sample mixture to provide a characteristic light emission; and
e. comparing the first sample fingerprint with the second sample fingerprint to determine relatedness of the two samples.

24. The method of claim 23, in which the first sample is identified as a specific product or as part of a homogeneous lot of a product by comparing the first sample mixture fingerprint to a library of fingerprint emission profiles of samples whose product composition or lot number are known.

25. The method of claim 23, further comprising providing an additional fingerprint emission profile for each of at least two additional samples and comparing the first sample mixture fingerprint to each of the additional fingerprint emission profiles.

26. The method according to claim 23, further comprising the steps of:

providing a mixture comprising ethanol and water; and evaporating substantially all the ethanol from the mixture to form the second sample.

27. The method according to claim 23, further comprising the steps of:

providing a mixture comprising ethanol and water; and evaporating substantially all the ethanol from the mixture to form the first sample.

28. The method according to claim 27, further comprising the steps of:

providing a mixture comprising ethanol and water; and evaporating substantially all the ethanol from the mixture to form the second sample.

29. The method of claim 1 or claim 23 wherein the method is used to determine product authenticity, product tampering, or product manufacturing compliance.

30. The method of claim 1 or claim 18 wherein the sample is a perfume, fragrance, flavor, food, or beverage product.

* * * * *